United States Patent [19]

Marder et al.

[11] Patent Number: 5,206,140
[45] Date of Patent: Apr. 27, 1993

[54] ASSAY FOR SOLUBLE CROSSLINKED FIBRIN POLYMERS

[75] Inventors: Victor J. Marder; Charles W. Francis, both of Rochester, N.Y.

[73] Assignee: Research Corporation Technologies, Inc., Tucson, Ariz.

[21] Appl. No.: 499,250

[22] Filed: Mar. 26, 1990

Related U.S. Application Data

[63] Continuation-in-part of Ser. No. 213,572, Jun. 24, 1988, abandoned.

[51] Int. Cl.⁵ .................. G01N 33/535; G01N 33/53; C07K 15/28; C12N 5/12
[52] U.S. Cl. ..................................... 435/7.1; 436/548; 530/388.25; 435/240.27
[58] Field of Search .................. 435/7.2, 7.91, 240.27, 435/7.1; 530/387, 388.25; 436/548

[56] References Cited

U.S. PATENT DOCUMENTS 4,563,420  1/1986  Verheijen et al. ..................... 435/13
4,710,459  12/1987  Bartl et al. ............................ 435/13

FOREIGN PATENT DOCUMENTS 0122478  10/1984  European Pat. Off. .
0173916  3/1986  European Pat. Off. .
8801514  3/1988  PCT Int'l Appl. .

OTHER PUBLICATIONS

Francis, et al., *Circulation*, 75:1170–1177 (1987).
Connaghan, et al., *British J. Haematology*, 61:564 (1985).
Connaghan, et al., *Blood*, 65:589 (1985).
Connaghan, et al., *Thrombosis and Haemostasis*, 54:165 (1985).
Wiman, et al., *Thrombosis and Haemostasis*, 55:189 (1986).
Lew, et al., *JACC*, 7:1320 (1986).
Francis, et al., *Circulation*, 74:1027 (1986).
Rylatt, et al., *Thrombosis Research*, 31:767–778 (1983).
Whitaker, et al., *J. Clin. Pathol*, 37:882–887 (1984).
Verheijen, et al., *Thrombosis Research*, 27:377–385 (1982).
Wiman, et al., *Clinica Chimica Acta.*, 127:279–288 (1983).
Olexa, et al., *Biochemistry*, 18 (6):991–995 (1979).
Declerck, P. J. et al., Thrombosis and Haemostasis, 58(4):1024–1029, 1987.
Greenberg, et al., Am J. Clin Pathology, 87:94–100, 1987.
Smith, G. F., Biochem J. 185:1–11, 1980.
Crabbe, S. J. et al., Clin Pharm. 6: 373–386, May 1987 (abstract).
Elms, M. J. et al., Thromb Haemostis, 50(2):591–594, 1983.

*Primary Examiner*—Merrell C. Cashion, Jr.
*Assistant Examiner*—Susan L. Futrovsky
*Attorney, Agent, or Firm*—Scully, Scott, Murphy & Presser

[57] ABSTRACT

This invention relates to an assay for fibrin polymers for use in the diagnosis of patients at risk of thrombosis and in monitoring the effects of treatment in such patients. More particularly, the present invention relates to an assay for soluble crosslinked fibrin polymers in patent samples involving the in vitro treatment of the sample with a proteolytic enzyme such as t-PA which generates the D-dimer fragment of soluble fibrin polymers. The amount of D-dimer formed is determined by an immunoassay specific for D-dimer. The measurement of D-dimer is thus a useful reflection of the hypercoagulability state and the test may be useful for assessing prethrombotic or thrombotic disorders such as myocardial infarction, pulmonary embolism and deep vein thrombosis, as well as for soluble fibrin formation in neoplastic, immune, inflammatory states, or other pathologic conditions, and for evaluations of therapy such as with anticoagulants that are used to treat these conditions.

17 Claims, 5 Drawing Sheets

ASSAY FOR SOLUBLE CROSSLINKED FIBRIN POLYMERS

The invention described herein was made in the course of work under a grant sponsored in part by the National Institutes of Health.

CROSS-REFERENCE TO PRIOR APPLICATION

The present application is a continuation-in-part of U.S. Ser. No. 213,572 filed Jun. 24, 1988, now abandoned.

FIELD OF THE INVENTION

The present invention relates to a novel assay for use in the diagnosis of patients at risk of thrombosis and in monitoring the effects of treatment of such patients. More particularly, the present invention relates to a novel method for measuring the amount of soluble crosslinked fibrin polymers involving the in vitro treatment of patient sample, e.g. plasma, with a plasminogen activator such as tissue-plasminogen activator (t-PA) or active plasmin to generate D-dimer products of soluble fibrin polymers, the amount of D-dimer generated being directly proportional to the amount of soluble crosslinked fibrin polymers in the patient sera, the amount being indicative of thrombin and factor XIII activation, i.e. on-going thrombosis, that may indicate a hypercoagulable state.

BACKGROUND OF THE INVENTION

Much effort has been expended in recent years to develop methods for measuring activation products of fibrinogen. The reason is that fibrinogen to fibrin conversion may be involved in many different pathological conditions, including the prethrombotic state and disseminated intravascular coagulation. Nevertheless, the presently available methods for direct determination of circulating fibrin (soluble fibrin) are not practical since they are either difficult to perform or suffer lack of sensitivity and of specificity. Such methods have consisted, among others, of chemical purification and chromatographic assay of soluble fibrin in human plasma or by a serial dilution protamine sulfate testing.

In theory, fibrin formation can be detected indirectly by determination of released fibrinopeptides. However, apart from being difficult to analyze, the fibrinopeptides have short half-lives and may not give the same information as direct determination of soluble fibrin.

It has also been proposed to use a method based on the stimulatory effect of fibrin obtained on the t-PA-catalyzed activation of plasminogen (Wiman et al., *Thrombosis and Haemostatis* 1986, 55:(2) 189). In this assay the t-PA activity increases in the presence of soluble fibrin and can be back-calculated to indicate soluble fibrin concentration. The end point determination, however, is one of enzymatic activity by t-PA on a plasmin-sensitive chromogenic substrate rather than a degradation fragment of the fibrin.

It has also been proposed to use immunoassays that utilize monoclonal antibodies raised against the unique antigenic determinants of crosslinked fibrin to specifically measure the degradation products of crosslinked fibrin without being influenced by the degradation products of fibrinogen (Rylatt et al. *Thromb. Res.* 1983, 31:767-78) (Whitaker et al., *J. Clin. Pathol.* 1984; 37:882-7) (Gaffney et al., *Thrombosis and Haemostasis* 1987; 58:231, abstract). The D-dimer is one of the degradation products of crosslinked fibrin which is stable and resists further digestion by plasmin. Elevated serum or plasma levels of D-dimer have been found in patients with pathologic fibrinolysis and after streptokinase-induced thrombolysis in patients with deep venous thrombosis or pulmonary embolus (Lew et al., *J.A.C.C.*, 1986, Vol. 1, No. 6, 1320-4). Therefore, this technique is potentially useful only for monitoring the end-product of fibrinolysis, for example, during physiologic thrombolysis or with therapy using plasminogen activators.

It would be highly desirable, therefore, to provide a rapid and simple assay that can be used for the in vitro measurement of soluble fibrin concentration, for example, in patient plasma as a useful reflection of the so-called "hypercoagulability state" or pre-thrombotic state reflecting an increased tendency to form fibrin. The assay should be for routine laboratory use and for the determination of large numbers of samples and with great accuracy.

A diagnostic immunoassay for measuring the increased reactivity of a test material for fragment D-dimer produced by the addition of a plasminogen activator to the sample, such as plasma, can be used to determine the original concentration of crosslinked fibrin polymer in the patient sample. Thus, the plasma concentration of D-dimer following degradation of soluble fibrin to D-dimer in vitro could be used as a simple indirect measure of circulating crosslinked fibrin polymer in the in vivo condition.

BRIEF SUMMARY OF THE INVENTION

The present invention provides a novel diagnostic assay having the foregoing advantages which involves the in vitro treatment of the patient sample with a plasminogen activator (such as t-PA) or active plasmin, to generate D-dimer. The results of this test could provide insight into and greatly facilitate the evaluation of patients with thrombosis or at risk of thrombosis and be highly useful in monitoring the effects of treatment of such patients. The amount of D-dimer formed is determined by an immunoassay specific for D-dimer. The amount of D-dimer generated is directly proportional to the soluble fibrin polymers present in patient samples which amount is indicative of thrombin and factor XIII activation, i.e. on-going thrombosis and may indicate a hypercoaguable state.

The present invention thus provides a means for practical determinations of patient samples in short time periods, is applicable for routine laboratory use and for the determination of large numbers of samples and with great accuracy. The materials needed are simple, easily transportable, applicable at large and small centers and even in doctor's offices and amenable to large scale automation. The use of crosslinked fibrin polymers as markers of hypercoagulability affords a very practical approach in that it deals with the final pathway toward clot formation, rather than dealing with intermediate steps in a complex coagulation pathway. Thus, the present invention provides an in vitro degradation to D-dimer that can be used as a simple indirect measurement of plasma crosslinked fibrin polymer concentration in patient samples. Such samples include but are not limited to blood, serum, plasma, urine, cerebrospinal fluid, ascites, exudate and transudate and in vitro fractions of such materials. The test can be useful for evaluating pre-thrombotic disorders which are associated with development of thrombi, and thrombotic disorders such as myocardial infarction, pulmonary embolism and deep vein thrombosis. Other pathologic conditions associated with fibrin formation, such as neoplasm, inflammatory and immunologic disorders, as well as the postoperative state and other trauma, and other miscellaneous pathologic states, may also be associated with elevated levels of crosslinked fibrin.

DETAILED DESCRIPTION OF THE INVENTION

The present invention is based upon the discovery that it is possible to provide an effective assay method to measure the amount of a proteolytic derivative, specifically fragment D-dimer (DD), generated by the degradation of soluble crosslinked fibrin polymers following the addition of a plasminogen activator, for example t-PA to a patient sample, e.g. plasma, in vitro. The degradation of crosslinked fibrin polymers to proteolytic derivatives induces molecular changes that can be exploited with simple detection techniques against fragment DD which is a well defined molecular entity that can be measured by various immunologic techniques using a specific antibody. Crosslinked fibrin polymers react little if at all in these immunologic systems and, therefore, the increased reactivity of a test material for fragment DD, after t-PA treatment, for example, of the material, bears a direct relationship to the original concentration of the crosslinked fibrin polymer in patient sample. Thus a quantitation of the original concentration of circulating crosslinked fibrin polymers in patient sample is achieved by an in vitro test which facilitates the diagnosis of patients at risk of thrombosis.

Under physiological conditions, fibrin formation is localized either intravascularly in the formation of hemostatic plugs or extravascularly in inflammatory foci. However, low concentrations of soluble fibrin circulate, and increased concentrations have been identified in patients with thrombotic disease reflecting a systemic effect of thrombin activity that can also be measured by plasma fibrinopeptide levels. Soluble fibrin also facilitates the thrombin cleavage of factor XIII to a transglutaminase which can form intermolecular covalent crosslinks between γ chain pairs of adjacent fibrin monomers. We have recently demonstrated (Francis et al., Circulation 1987; 75:1170-1177) a low concentration of γ chain crosslinked fibrin dimer in plasma of normal individuals and a significant increase in patients presented with acute myocardial infarction.

Pharmacologic stimulation of fibrinolysis in the treatment of thrombotic disease results in a variable degree of degradation of circulating fibrinogen in addition to the desired effect of thrombolysis. Because the γ chain isopeptide crosslink in stabilized fibrin renders this portion of the molecule resistant to plasmic degradation, plasmic degradation products of crosslinked fibrin differ structurally from those of fibrinogen. As stated hereinbefore this difference has been exploited in the development of several methods to measure circulating crosslinked fibrin-specific degradation products as potential markers of clot lysis. The present invention utilizes antibodies specific for crosslinked fibrin degradation products in quantitative immunologic assays.

Antibody DD-3B6/22 (Rylatt et al. and Whitaker et al., supra) that is directed toward an epitope near the γ crosslink site present in crosslinked fibrin degradation products such as fragment DD is preferably used in the present process, but other antibodies reactive preferentially with D-dimer or other degradation products rather than with fibrin could also be used. Since crosslinked fibrin polymers and crosslinked fibrin degradation products both contain the γγ crosslink, the possibility exists that both would react with this antibody. However, this potential problem is not the case, as demonstrated below (see experiment). Crosslinked fibrin polymer formation is induced in vitro by exposure of plasma to low concentrations of thrombin; the reactivity of soluble fibrin polymers is assessed in an enzyme-linked immunosorbent assay (ELISA) using a monoclonal antibody reactive with the γγ chain crosslink. In addition, t-PA-treated samples of plasma and thrombin-exposed plasma, in which fibrin is converted to D-dimer, are assessed for reactivity in the same immunoabsorbent assay with antibody against γγ chain crosslink. The changes in immunoreactivity with thrombin-induced formation of fibrin polymers and with t-PA-induced degradation have important implications for interpreting studies of fibrin and fibrinogen degradation products during thrombolytic therapy and for the development of assays to detect plasma crosslinked fibrin polymers.

Rylatt, et al., have provided the following procedure for making monoclonal antibody DD/3B6/22 against D-dimer:

MATERIAL AND METHODS

Preparation of Antigens

Fibrinogen was prepared as described by Laki (13) except that the plasma was first absorbed with lysin sepharose (14) and barium chloride (15) to remove plasminogen and prothrombin followed by precipitation with 2.5 M glycine to remove factor XIII (16). Other modifications included ion exchange chromatography on DEAE-Sepharose (pharmacia, Uppsala, Sweden) and gel filtration on Sephacryl S300 (Pharmacia). Fibrinogen degradation products (X Y D E) were formed by the lysis of 30 mg/ml fibrinogen with 0.04 I.U. plasmin/mg fibrinogen for 30 min at 25° C. in a buffer containing 150 mM Tris acetate, and 10 mM Calcium Chloride pH 7.4. Purified fragment $D_{cate}$ (17) was prepared after digestion of fibrinogen (186 mg.ml) with 7.24 units/ml plasminogen and 1000 I.U./ml streptokinase in 50 mM Tris acetate 10 mM Calcium Chloride pH 8.6 for 18 h at 25° C. and subsequent dialysis, ion exchange chromatography on DEAE cellulose (Whatman) and gel filtration on Sephacryl S300. Fragment E was purified by the method of Nilehn (18). Crosslinked fibrin degradation products were prepared essentially as described by the methods of Francis et al (19) and Olexa and Budzynski (20) except that lysis was carried out in buffers containing 40 mM Calcium Chloride. The lystate contained high molecular weight crosslinked derivatives, D dimer, D dimer-E and fragment D. Purification of D dimer was achieved by chromatofocussing using PBE 94 and poly buffer 74 (Pharmacia). D dimer eluted as an early peak separate from D dimer-E, D and E. After rechromatography on Sepharose CL4B (Pharmacia) D dimer was stored in 50% plycerol at −202 C. Protein determination was carried out by the method of Rylatt and Parish (21).

Immunization and Hybridoma Production

Eight week old female BALB/c mice were injected subcutaneously 3 times at 2 weekly intervals with 0.1 ml of a preparation of 12.5 ug total crosslinked fibrin lysate in Freund's complete adjuvant. Four weeks after the last injection, 2 mice were boosted with an intraperitoneal injection of 10 ug D dimer in 0.5 ml PBS. Three days later the mice were killed and a pooled spleen cell suspension was prepared and fused with NS-1 myeloma cells (22). Selected crude clones, chosen on the basis of the screening assay were subcloned by limiting dilution and subsequently a number of MAb secreting hybridoma cell lines ere finally chosen for expansion to mass culture and for the production of ascitic fluids.

Female BALB/c mice were given an intraperitoneal injection of 0.5 ml 2, 5, 10, 14, tetramethylpentadecane (Pristane, Aldrich Chemical Corp., Milwaukee, Wisc.) 14 days prior to the injection of $2 \times 10^6$ viable hybridoma cells and ascites fluids were collected from the mice 12 to 14 days after injection of the cells. The ascitic fluid was clarified by centrifugation and MAb were recovered by precipitation with 45% ammonium sulphate and stored at either 4° C. or −70° C. in phosphate buffered saline (PBS) containing 0.01% sodium azide. Conjugation of MAb was carried out essentially as described by Nakane and Kaiwoi (23) except that the reaction was terminated by the addition of ethanolamine (24).

MAb Screening Assay

The wells of a 96 well U bottomed microtitre plate (Disposable Products Pty Ltd, Adelaide, South Australia) were coated by adding 50 ul of either D dimer (5 ug/ml) or fibrinogen degradation products (5 mg/ml) in PBS for one hour at room temperature (25° C.). Excess antigen was removed by inverting and tapping the plate and the plate was then washed three times with PBS containing 0.05% Tween 20 (PBS/Tween; Tween 20, Sigma Chemical Corp., St. Louis, Mo.). Clones secreting MAb to D dimer or fibrinogen degradation products were then detected by adding 50 ul of tissue culture supernatant to each well and incubating for one hour at room temperature. Unbound MAb was removed by inversion and tapping and the plate was washed three times with PBS/Tween. One hundred ul of a 1/1000 dilution of peroxidase conjugated rabbit anti-mouse immunogloublin (Dakopatts, Copenhagen, Denmark) in PBS/Tween was added and allowed to incubate a further one hours at room temperature. The plate was then inverted and washed three times with PBS/Tween and 100 ul of activated substrate was added to each well. The substrate was activated immediately before use by adding 10 ul of a 3% solution of $H_2O_2$ to 10 ml of the substrate solution containing 10 mM citrate, 2.5 mM O-tolidine dihydrochloride (O-tolidine, Sigma Chemical Co., recrystallized from dilute HCl), 0.025 mM EDTA PH 4.5. The colour reaction was stopped after 10 minutes by the addition of 50 ul of 3 M HCl which caused a colour change from blue to yellow and the absorbance was recorded at 450 nm on a Titertek multiskan.

Capture/Tag Experiments

Antigen capture/tag experiments were performed by incubating each well of a 96 well microtitre plate with 50 ul (10 ug/ml) of each of the relevant MAb in PBS for 1 hour at room temperature. Unbound MAb was removed by inverison and tapping the palte followed by washing with PBS/Tween as described for the screening assay. Antigen capture was then achieved by adding 50 ul of each antigen (0–1 mg/ml) in PBS/Tween to the MAb coated well for 1 hour at room temperature. The wells were washed as previously described. Captured antigen was then tagged with peroxidase conjugated MAb by adding 50 ul (1 ug/ml) of the various perioxidase conjugated MAb in PBS/Tween to each well for 1 hour at room temperature. After washing, the presence of bound conjugate was determined by the addition of 100 ul substrate as described in the screening assay. For the determination of the presence of crosslinked derivatives in plasma or serum, 50 ul of a 1/5 dilution of plasma or serum in PBS/Tween was incubated instead of antigen at the second step.

RESULTS

Specificity

Several hundred hybridoma clones secreting MAb against human D dimer were initially identified by enzyme immunoassay and two different classes of MAb were obtained (TABLE 1). The first group which contained the vast majority of positive clones (examples of which were DD-4D2/182, DD-2C1/19, DD-2D5/38), produced MAb that bound to epitopes present on intact fibrinogen, fibrinogen degradation product $D_{cate}$, fibrin breakdown product D dimer but not present on fragment E. The second and much smaller group (examples of which were DD-3B6/22 and DD-1C3/108), reacted with determinants present on D dimer but not on fragment $D_{cate}$.

The present invention relates to a process for the in vitro determination of crosslinked soluble fibrin polymers. In one embodiment, this process involves contacting the sample with at least one proteolytic enzyme to generate the D-dimer fragment of the fibrin polymers and subsequently measuring the amount of the D-dimer, for example, by the use of an immunoassay specific to the D-dimer. Other conventional means are also contemplated, such as gel electrophoresis, thin-layer chromatography, and column chromatography. In another preferred embodiment, this process involves adding a plasminogen activator (such as t-PA) to the sample in order to activate endogenous fibrin-bound plasminogen, which is then converted to plasmin. This plasmin in turn breaks down the soluble fibrin polymers in order to generate the D-dimer fragment of the fibrin polymers. In another aspect, plasminogen and a plasminogen activator (such as t-PA) can be added together to the samples. A preferred amount of plasminogen which would then be added to the samples is in the range of from about 1 unit/ml to 10 units/ml. As a result of this addition, t-PA levels can be reduced to as low as 10 ug/ml.

In the further detailed description and example which follow, it should be noted that the following materials and methods were used:

Proteins. Human fibrinogen (grade L) was purchased from Helena Laboratories (Beaumont, Tex.) and was 93% clottable. Fibrinogen concentration was determined by measurement of optical density at 280 nm using an extinction coefficient of 15.1. Human thrombin (3200 NIH U/mg) was purchased from Calbiochem-Behring Corp. (La Jolla, Calif.), hirudin and bovin serum albumin were from Sigma Chemical Co. (St. Louis, Mo.), aprotinin from Mobay Chemical Co. (New York, N.Y.), and tissue plasminogen activator (100,000 IU/mg) from Burroughs Wellcome Co. (Research Triangle Park, N.C.). Goat anti-human fibrinogen IgG was obtained from Cappel Laboratories (Cochranville, Pa.). Purified factor XIII concentrate (Fibrogammin), prepared from human placenta, was provided by Behringwerke/Hoechst-Roussel (Somerville, N.J.). Factor XIII was assayed by dansyl cadaverine incorporation into casein and the activity expressed in relation to pooled normal plasma defined as 100%.

Radiolabeling. Fibrinogen was labeled with the iodogen technique to a specific activity of 0.05 mCi/mg using 0.02 mg iodogen and 100 uCi $^{125}$I per ml of fibrinogen (20 mg/ml). Labeled fibrinogen was 93% clottable and showed the same electrophoretic mobility on SDS, 7% polyacrylamide gel electrophoresis after disulfide bond reduction. Goat antihuman fibrinogen IgG was radioiodinated to a specific activity of 0.4 mCi/mg using the lactroperoxidase method (Marchalonis. J.J., *Biochem J.*, 1969; 113:299). Bound and free iodine were separated after labeling by chromatography on Sephadex G-25 (Pharmacia Fine Chemicals, Piscataway, N.J.).

Preparation of fibrin polymers. Fibrinogen was dissolved to a final concentration of 10 mg/ml, calcium chloride added to a final concentration of 0.025 mol/L and factor XIII to a concentration of 12 units/ml. Thrombin was then added at a final concentration of 0.0025 units/ml, the solution was incubated at 37° C. for intervals of 10 to 45 min, and the thrombin activity was inhibited by addition of hirudin to a final concentration of two units/ml.

Blood Samples. After obtaining informed consent, blood was collected from normal volunteers into sodium citrate (0.4% final concentration) and plasma separated from red cells after centrifugation at 3500 g for 15 min. at 4° C.

Electrophoretic Analysis. Fibrinogen and fibrin derivatives were identified in plasma after SDS 2% agarose electrophoresis (Connaghan, D.G. 1985; *Blood* 65:5891). Plasma was prepared for electrophoresis by diluting 1:20 in 0.01M phosphate buffer, pH 7, containing 1.7% SDS and heating at 100° C. for 5 min or 60° C. for one hour. Samples of 10 μl were electrophoresed at 150 volts on a flat bed electrophoretic apparatus (Pharmacia Fine Chemicals, Piscataway, N.J.) with cooling to 10° C. Electrophoresis was allowed to proceed until the tracking dye had migrated 10 cm. Gel scanning was performed with a Quik-Scan Jr. (Helena Laboratories, Beaumont, Tex.).

Western blotting was performed using a modification of the method of Towbin and colleagues (*Proc. Nat'l Acad. Sci. USA* 76:4350, 1979), using a Transblot Cell (BioRad Laboratories, Richmond, Calif.). Transfer to nitrocellulose paper (pore size 0.2 um, Schleicher and Schuell, Keene, N.J.) was done in 0.01M Tris hydrochloric buffer, pH 8.3 containing 0.096M glycine and 20% (v/v) methanol at 60 volts for 3 hrs at 20° C. The nitrocellulose paper was incubated at 3° C. for 24 hrs in 0.05M phosphate buffer, pH 7.3, containing 0.15M sodium chloride and 3% (w/v) bovine serum albumin. This was removed, and the paper was incubated for 2 hrs at 20° C. with gentle rocking with 50 ml of 0.05M phosphate buffer, pH 7.3, containing 0.15M sodium chloride, 3% (w/v) bovine serum albumin and 0.05% (v/v) Tween 20 and $2 \times 10^{-5}$ Ci $^{125}$I-labeled goat anti-human fibrinogen IgG. The nitrocellulose paper was then washed with 6 volumes of 40 ml each of 0.05M phosphate buffer, pH 7.5, containing 0.15M sodium chloride and 0.05 (v/v) Tween 20 using gentle agitation on a platform shaker for 10 min for each wash. Following drying, the paper was processed for autoradiography using Kodak X-Omat film (Eastman Kodak, Rochester, N.Y.) with exposure times up to 72 hrs.

ELISA. Crosslinked fibrin degradation products were measured with an ELISA (Dimer Test, American Diagnostica, Greenwich, CT) employing a monoclonal antibody (DD/3B6) reactive with a site near the factor $XIII_a$ mediated crosslink (Rylatt et al. and Whitaker et al., supra). Precoated plates were used and results calculated using a standard curve prepared with purified fragment DD provided by the manufacturer at concentrations from 40 ng/ml to 5000 ng/ml. Plasma was assayed undiluted prior to incubation with t-PA and at 1:5 dilution after incubation.

The invention will be described in greater detail in conjunction with the following specific example.

EXAMPLE

Figure 1:
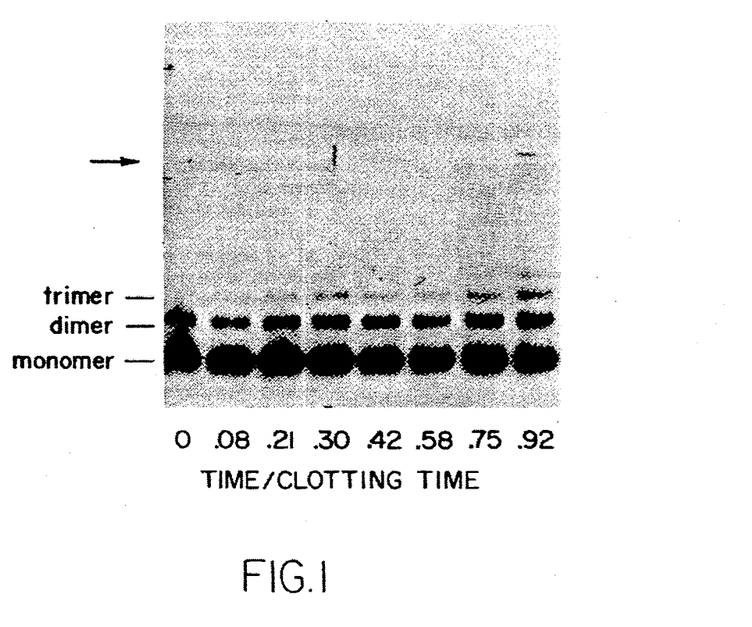
FIG. 1 shows the crosslinked fibrin polymers in plasma following addition of thrombin.

The addition of a low concentration of thrombin to normal plasma (0.025 U/ml final concentration) results in a progressive increase in crosslinked fibrin polymers before clot formation, as shown in the autoradiogram (FIG. 1). Prior to thrombin addition (time 0), bands corresponding to fibrin dimer and a trace of trimer are present in the $^{125}$I radiolabeled fibrinogen. After thrombin addition, but prior to clot formation, the dimer band becomes more prominent and larger polymeric forms are seen. The greatest change occurs in the last sample prior to clotting (at 0.92 clotting time), when up to six polymeric forms can be seen and some protein fails to enter the 2% agarose gel.

The formation of crosslinked fibrin polymers in plasma following addition of thrombin is shown in FIG. 1. Pooled normal citrated plasma containing $^{125}$I radiolabeled fibrinogen is incubated with thrombin (0.025 U/ml final concentration) and calcium chloride (10 mM final concentration). At intervals, aliquots are withdrawn and prepared for electrophoresis by diluting 1/20 is SDS containing diluent and heating at 60° C. for one hour. Samples of 10 μl are electrophoresed and the autoradiogram prepared following drying with an exposure time of 3 days. Time/clotting time indicates the time at which the sample is withdrawn divided by the observed clotting time. The arrow indicates the location of application wells.

Figure 2:
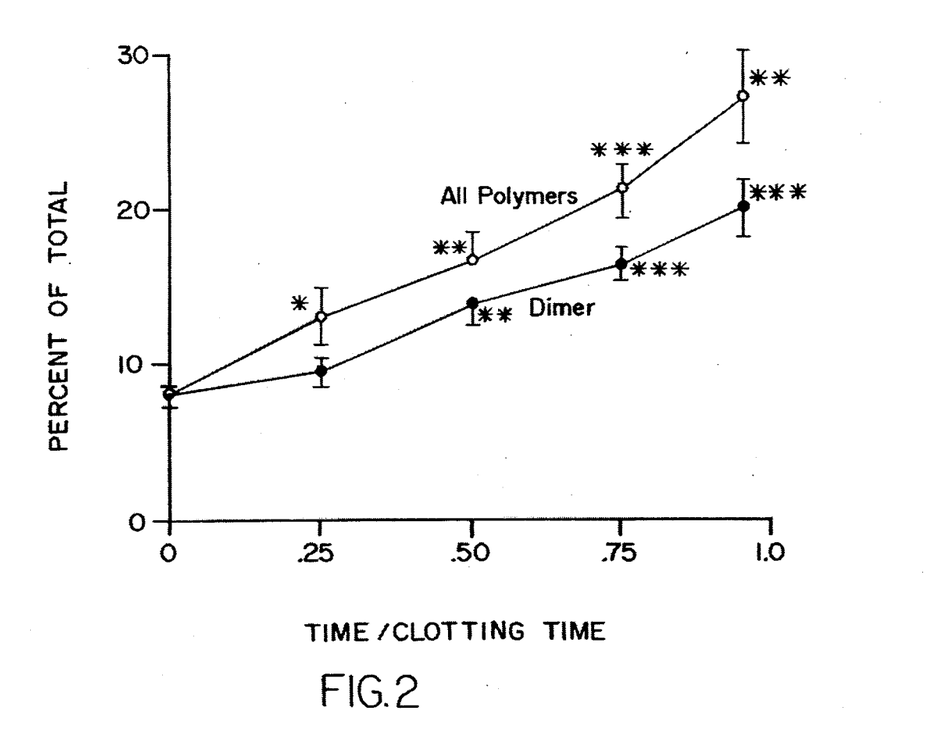
FIG. 2 shows the quantitation of increase in crosslinked fibrin polymers in plasma after thrombin addition relative to clotting time.

The use of $^{125}$I radiolabeled fibrinogen allows accurate quantitation of fibrin polymer formation by slicing the fixed gel after staining and electrophoresis and then counting individual slices to determine the proportion of each polymer band (FIG. 2). Prior to the addition of thrombin, 8% of the radiolabel migrates as crosslinked dimer and 8.2% as dimer plus larger polymers. The proportion of crosslinked polymer increases progressively following addition of thrombin, with a peak of 20% dimer and 27% total crosslinked polymer present just prior to visible fibrin formation. A statistically significant increase in dimer concentration occurs by 0.5 clotting time and in total crosslinked polymer concentration at 0.25 clotting time. Polymeric forms larger than dimer are most abundant immediately prior to visible clot formation at 0.9 clotting time when they represent 7% of the total. No increase in polymer formation is seen when the same experiment is performed using plasma anticoagulated with EDTA (0.1% final concentration) and without added calcium chloride.

FIG. 2 shows in detail the quantitation of increase in crosslinked fibrin polymers in plasma after thrombin addition relative to clotting time. Thrombin (0.025 to 0.1 u/ml, final) and calcium chloride (10 mM final) are added to pooled normal plasma containing $^{125}I$ radiolabeled fibrin. Aliquots are withdrawn at intervals prior to clot formation during incubation at 37° C. and prepared for electrophoresis. Following staining with Coomassie Blue, bands corresponding to monomer, dimer and larger polymers are cut from the gel and counted. Time/clotting time indicates the time of withdrawal of the sample divided by the final clotting time. Statistically significant increases in comparison with time 0 values are indicated: *, $p<0.05$; , $p<0.01$; *, $p<0.005$.

Figure 3A:
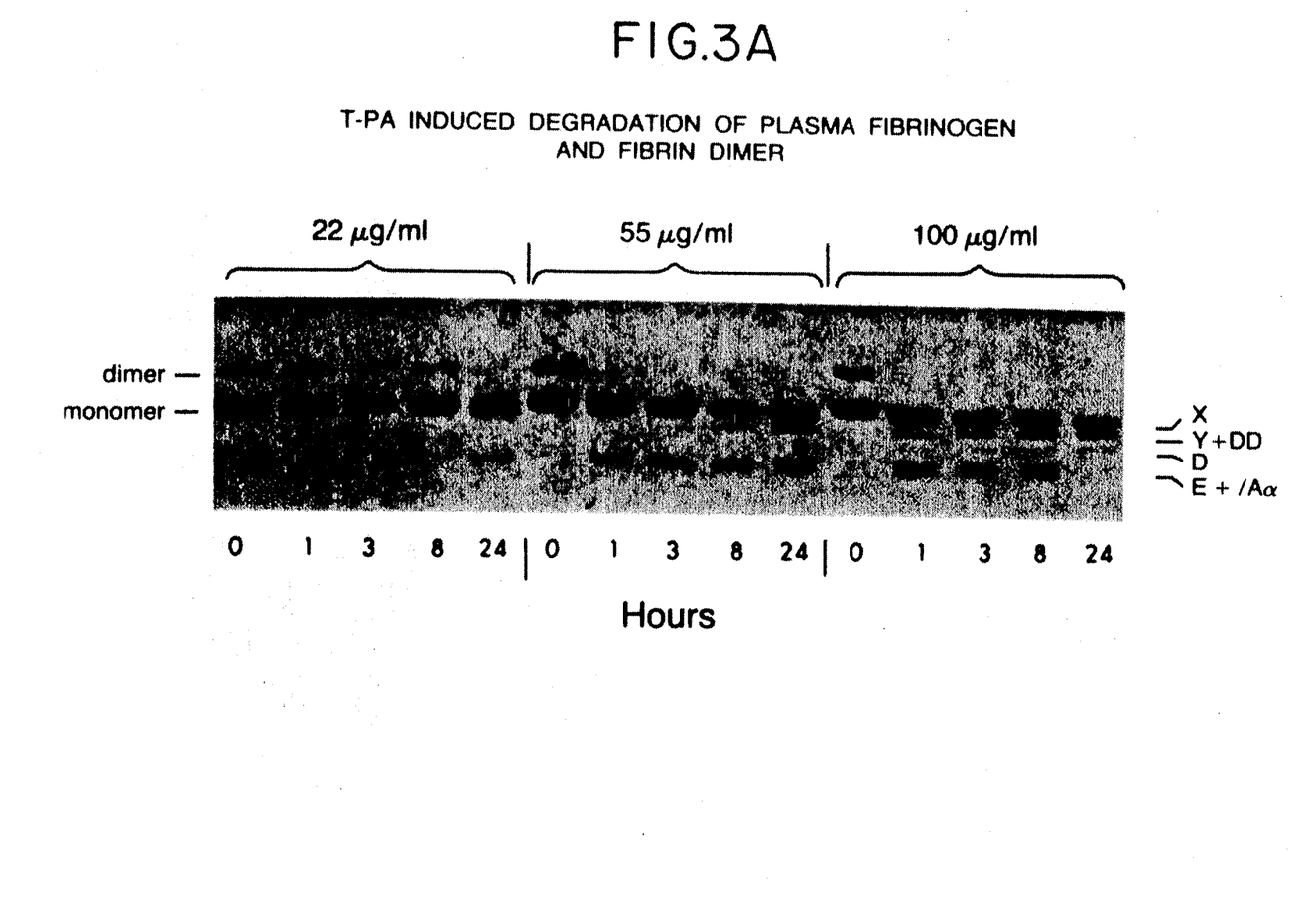
FIG. 3A shows t-PA-induced degradation of fibrinogen and crosslinked fibrin polymers in plasma.
Figure 3B:
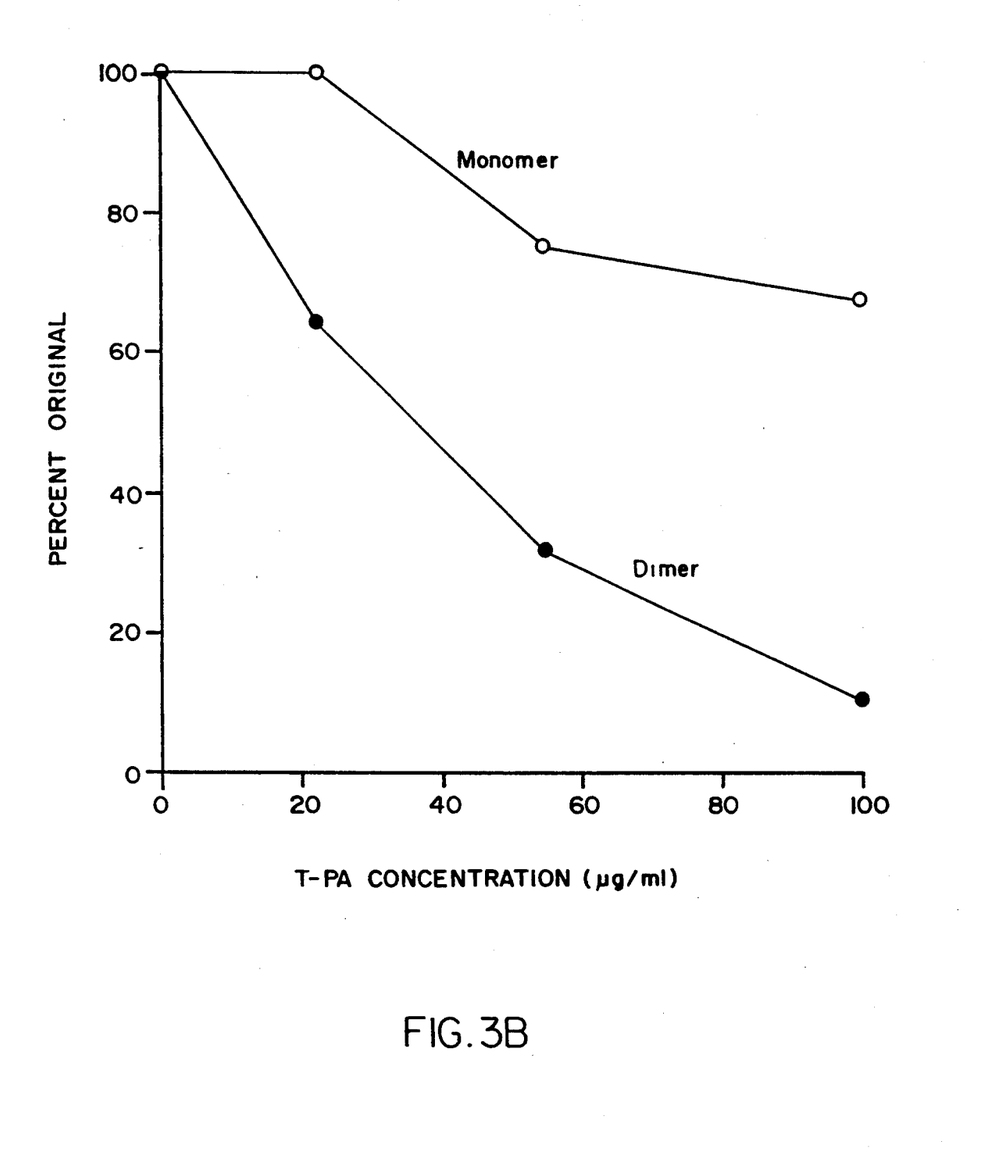
FIG. 3B is a comparison of rates of plasmic degradation of fibrin dimer and fibrinogen/fibrin monomer.

Plasmic degradation of soluble crosslinked fibrin polymers is followed electrophoretically after addition of t-PA to normal plasma to which a preparation of $^{125}I$ radiolabeled fibrin polymer is added (FIG. 3). At 16 ug/ml t-PA the fibrinogen band does not change, but the dimer band is fainter at 24 hrs and migrates further, consistent with degradation to fragment XX. At 55 and 100 µg/ml t-PA, fibrinogen is degraded to fragment X within the first three hours but then persists during longer incubations, showing little cleavage to smaller fragment Y, D and E. In contrast to the plasmic resistance of fibrinogen and fragment X, the degradation of the crosslinked fibrin dimer occurs rapidly. At 55 µg/ml and 100 µg/ml t-PA, most fibrin dimer is degraded by one hour with little dimer or fragments larger than fibrinogen remaining after longer incubations. The rates of degradation of fibrin dimer and fibrinogen are compared following gel scanning, and at all concentrations of t-PA tested, degradation of the dimer is more rapid than the monomer (FIG. 3B). At 16 µg/ml t-PA, there is no decrease in the monomer at 3 hrs while the dimer has decreased to 64% of original. The difference in degradation between monomer and dimer is greater at higher enzyme concentrations with only 10% of dimer remaining at 3 hrs at 100 µg/ml t-PA compared to 68% of monomer.

t-PA-induced degradation of fibrinogen and crosslinked fibrin polymers are shown in FIGS. 3A and 3B. Tissue plasminogen activator at concentrations of 16 µg/ml, 55 µg/ml, and 100 µg/ml are added to pooled normal plasma containing an $^{125}I$ radiolabeled preparation of crosslinked fibrin polymers. During incubation at 37° C., aliquots are withdrawn at the indicated times and prepared for electrophoresis. Following staining and drying, the autoradiogram is exposed for six days. The 2% agarose gel system has limited resolution of fragments smaller than fibrinogen; fragments Y and DD overlap and cannot be resolved and Fragment E migrates with degradation products of the A chain.

FIG. 3B shows a comparison of rates of plasmic degradation of fibrin dimer and fibrinogen/fibrin monomer. The lanes in FIG. 3A corresponding to the three hour t-PA incubation are scanned, and the rate of degradation of fibrin dimer and fibrinogen/fibrin monomer are calculated in comparison with the time 0 sample. Since the gel system does not distinguish between fibrinogen, fibrin monomer and fragment X, these are measured together, and the decrease shown represents coiled-coil cleavage to smaller fragments Y, D, or E. Similarly, since plasmic derivatives smaller than fibrin dimer but larger than fibrinogen are difficult to measure separately using the gel scanning technique, the value for fibrin dimer represent all bands larger than fibrinogen, thereby tending to overestimate the remaining fibrin dimer.

TABLE 1

Concentration of D-dimer by ELISA in pooled normal plasma after one hour incubation with t-PA (mean of 2 experiments)

| t-PA concentration µg/ml | Plasma D-dimer concentration ng/ml |
| --- | --- |
| .001 | 100 |
| .01 | 325 |
| .1 | 350 |
| 1 | 500 |
| 10 | 1000 |
| 100 | 2700 |
| 400 | 2700 |

Since plasma crosslinked fibrin polymers increase after thrombin exposure, and plasmic degradation of polymers produces fragment DD, fragment DD is quantitated following incubation of plasma with t-PA before and after thrombin treatment to determine the effect of increased fibrin polymers on the apparent D-dimer concentration, before and after plasmic degradation by t-PA. The plasma D-dimer reactivity increases after in vitro treatment with t-PA for one hour in a concentration-dependent manner, reaching a plateau above 100 µg/ml of t-PA (Table 1).

Figure 4:
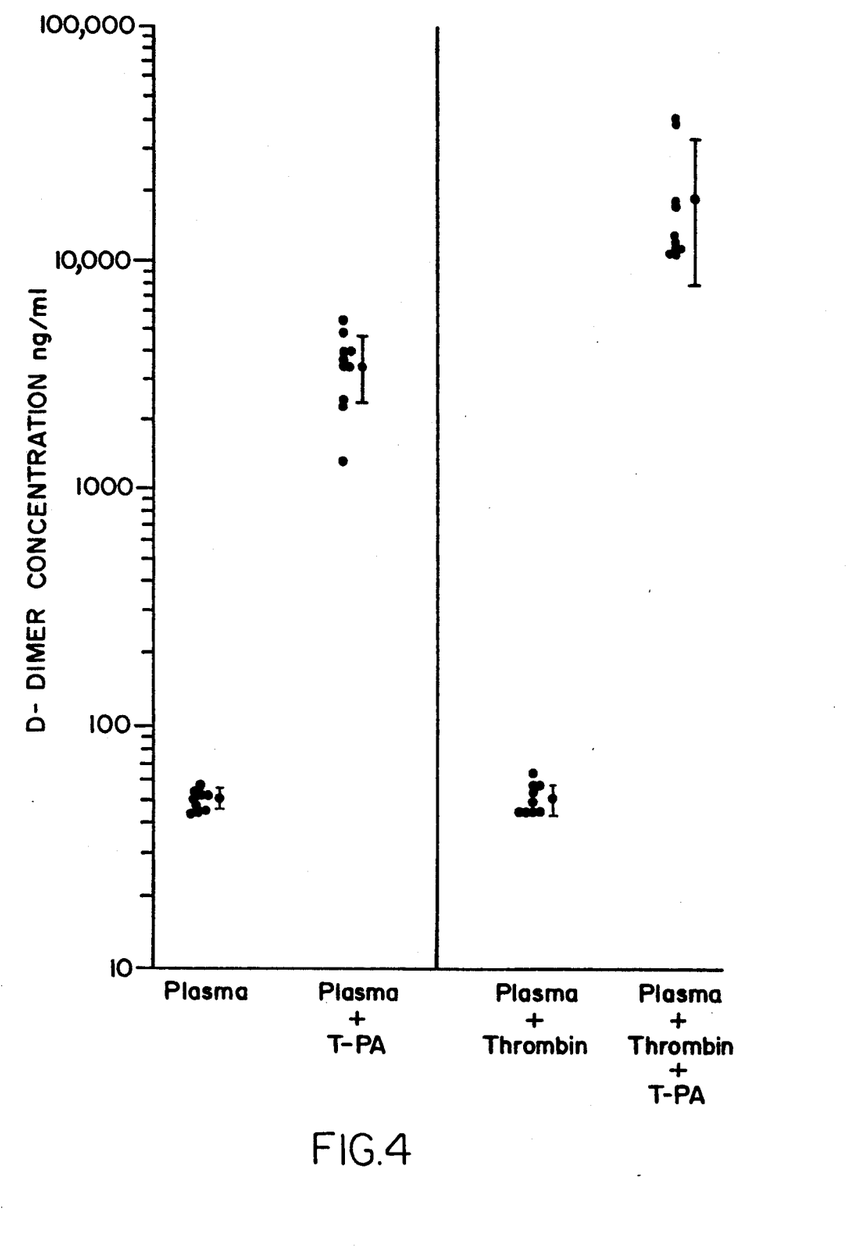
FIG. 4 shows plasma immunoreactivity in a D-dimer ELISA assay before and after treatment with thrombin and/or t-PA.

The mean D-dimer concentration in normal citrated plasma is $50.3\pm4.5$ ng/ml, with no change after incubation with thrombin (0.05 units/ml final concentration) for 20 min at 25° C. (FIG. 4). The DD concentration increases markedly to a mean of $3,560\pm1235$ ng/ml after incubation with t-PA (200 µg/ml). Following exposure to thrombin, t-PA incubation produces an even larger increase in D-dimer concentration to a mean of $18,580\pm11,780$ ng/ml. An increase in the DD concentration following t-PA digestion occurs in all plasma samples with no overlap between those digested before and after thrombin treatment.

FIG. 4 shows plasma immunoreactivity in a D-dimer ELISA assay before and after treatment with thrombin and/or t-PA. D-dimer concentration in citrated plasma collected from 10 normal individuals is $50.3\pm4.5$ ng/ml (mean$\pm$SD) (left); after incubation with t-PA (200 µg/ml, final concentration) for one hour at 37° C., the concentration is $3,560\pm1,238$ ng/ml. The same plasmas are also incubated with thrombin (0.05 u/ml final concentration) for 20 min at 37° C. Prior to incubation with t-PA, there is no change in D-dimer reactivity ($51.5\pm7.5$) ng/ml, but values for all samples increase markedly following t-PA incubation to a mean of $18,580\pm11,780$ ng/ml.

Figure 5:
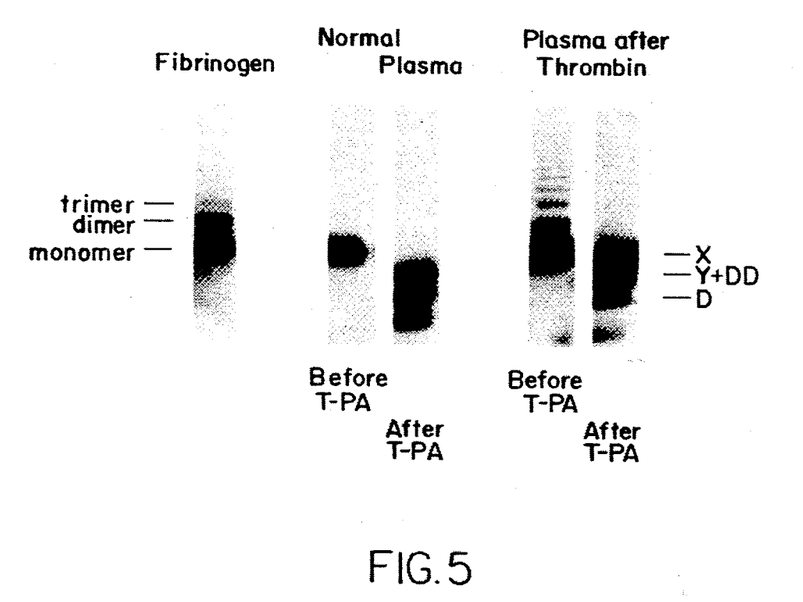
FIG. 5 shows the changes in plasma fibrinogen after incubation with thrombin and/or t-PA.

The changes after thrombin and t-PA are reflected in the gel pattern seen after Western blotting with antifibrinogen antiserum (FIG. 5). Normal plasma shows a heavy fibrinogen and faint dimer band; after thrombin exposure, more dimer is seen and bands corresponding to five larger crosslinked polymers are present. Following incubation with t-PA, bands corresponding to polymers are absent, confirming complete degradation, and only fragments smaller than fibrinogen are present.

FIG. 5 shows changes in plasma fibrinogen after incubation with thrombin and/or t-PA. A single normal plasma sample is treated as in FIG. 4 with thrombin (0.05 U/ml for 20 min at 37° C.), t-PA (200 μg/ml for 1 hr at 37° C.) or thrombin followed by t-PA. Following SDS 2% agarose gel electrophoresis, Western blotting is performed using an antifibrinogen antiserum.

The foregoing experiments demonstrate several effects on plasma fibrinogen resulting from exposure to a low concentration of thrombin and/or activation of fibrinolysis by t-PA. First, there is a progressive and significant increase in soluble crosslinked fibrin polymers prior to clot formation in vitro (See FIGS. 1 and 2) resulting from the combined action of thrombin and factor XIII. Second, fibrin polymers are degraded more rapidly than fibrinogen (FIG. 3), indicating that the fibrin specificity of t-PA, demonstrated with insoluble fibrin, is retained by the soluble crosslinked fibrin polymers. Third, monoclonal antibody DD/3B6, reactive with the γ chain crosslinked epitope in fragment DD, does not react with the same crosslinked γ chain site in fibrin polymers as indicated by the same reactivity of plasma before or following thrombin addition (FIG. 4). This indicates either that the crosslink site is obstructed from the antibody or that additional confirmational features associated with degradation are critical in determining antibody reactivity with DD/3B6. Fourth, degradation products of plasma soluble fibrin are recognized by the antibody (FIGS. 4 and 5); therefore, fragment DD present in blood may derive from such polymers as well as from dissolved clot.

Using several techniques, low concentrations of soluble fibrin have been found in normal plasma, with increased amounts in thrombotic disease. Plasma fibrinopeptide A concentration, elevated in thrombotic diseases, reflects the action of thrombin in cleaving fibrinopeptide A from fibrinogen and is a sensitive marker of systemic thrombin action but an indirect measure of plasma soluble fibrin. A concentration of soluble fibrin in normal plasma of 0.6 to 0.7 mg/dl and a 10-fold increase after acute myocardial infarction has been found using fibrinogen affinity chromatography to purify fibrin molecules containing the gly-pro-arg site exposed by thrombin cleavage. An increase in soluble fibrin in patients with stroke or myocardial infarction has been infered by an increase in large early eluting fibrinogen antigen after gel filtration chromatography.

The crosslinked fibrin polymers identified in FIGS. 1 and 2 require the additional action of factor XIIIa to crosslink the γ chains of fibrin monomers. Several factors support the concept of such coordinated action of thrombin and factor XIII$_a$ during activation of coagulation. During spontaneous clotting of plasma in vitro, cleavage of fibrinopeptides and activation of factor XIII are closely related events. The binding of both thrombin and factor XIII to fibrin may explain the enhancement of thrombin-catalyzed factor XIII$_a$ formation by fibrin polymers in plasma. Prior studies have provided indirect evidence for circulating crosslinked fibrin polymers by identifying γ chain dimers in extracts of plasma obtained from patients with thrombotic disease. Using an electrophoretic technique we have demonstrated directly a low concentration of crosslinked fibrin dimer in normal plasma and a significant elevation in patients with acute myocardial infarction.

Tissue plasminogen activator has a high affinity for fibrin and preferentially activates fibrin-bound plasminogen, properties serving to localize physiologic fibrinolysis and also forming the theoretical basis for the relative fibrin selectivity of t-PA as a therapeutic agent. Soluble fibrin also stimulates activation of plasminogen by t-PA and this observation has been exploited as a potential method of measuring soluble fibrin. Thus we have demonstrated preferential degradation of soluble crosslinked fibrin dimer compared to monomer (FIG. 3), consistent with the fibrin specificity of t-PA. Although the relative affinity of t-PA for solid fibrin compared to soluble crosslinked fibrin polymers is not known, it appears that therapeutic administration of t-PA would result in degradation of crosslinked fibrin polymers in preference to fibrinogen. Crosslinked fibrin polymers would be the initial component of plasma "fibrinogen" to be degraded during development of the systemic lytic state after t-PA administration.

The degradation of soluble crosslinked fibrin polymers has to be considered in evaluating results of assays for "fibrin-specific" degradation products, particularly in the setting of fibrinolytic therapy. While the monoclonal antibody directed against the γ chain crosslink epitope appears to have little reactivity with this site in soluble crosslinked fibrin, plasmic degradation of the fibrin increases immunoreactivity markedly (FIG. 4). With administration of a fibrinolytic agent such as streptokinase, marked degradation of plasma fibrinogen occurs. A concomitant degradation of plasma crosslinked fibrin polymer probably occurs with a resultant elevation in plasma D-dimer. The plasma fibrinogen also decreases with administration of fibrin selective agents such as t-PA and, since plasma crosslinked fibrin polymers degrade preferentially over fibrinogen (FIG. 3), an increase in plasma D-dimer would be expected in this circumstance as well. Administration of t-PA to normals has been reported to increase plasma D-dimer levels to 980 ng/ml as measured by an ELISA using antibodies different from those employed herein (Declerck, P. et al., Thromb. Haemost 58:231, 1987). After thrombolytic therapy for acute myocardial infarction, a wide range of D-dimer concentrations from 1500 ng/ml to 10,732 ng/ml has been reported using various techniques. The data presented herein (FIG. 4) suggests that a large part of these elevations could derive from degradation of soluble crosslinked fibrin polymer. In contrast, the higher levels of 24,200 ng/ml and 64,000 ng/ml measured after fibrinolytic therapy for deep vein thrombosis and up to 100,000 ng/ml for pulmonary embolism could not originate entirely from plasma soluble fibrin polymers and would require additional crosslinked fibrin degradation products from lysis of thrombus.

Thus, the plasma concentration of D-dimer following t-PA degradation in vitro can be used as an indirect measure of circulating crosslinked fibrin polymer. Fragment DD with $M_r$ 195,000 represents 30% of a fibrin dimer with $M_r$ 680,000. In patients presented with acute myocardial infarction we have found using an electrophoretic technique a plasma concentration of fibrin dimer of 3.6–4.0% compared to 0.8% in normals. This observation of 3,560 ng/ml D-dimer after t-PA degradation of plasma in vitro (FIG. 4) would require an initial 11,867 ng/ml of crosslinked fibrin dimer, an amount that could be provided by degradation of plasma fibrin polymer representing only 0.4% of total plasma fibrinogen (3 mg/ml), compatible with prior measurements in normals. Similarly, after thrombin exposure in vitro the value of 18,580 ng/ml (FIG. 4) would derive from 61,900 ng/ml plasma crosslinked fibrin, representing 2.1% of plasma fibrinogen. These values make it clear that an in vitro degradation to D-dimer can be used as a simple indirect measure of plasma crosslinked fibrin polymer concentration as described hereinbefore.

It is to be understood that a variety of plasminogen activators may be used in this invention to generate D-dimer products. In general, any proteolytic enzyme such as streptokinase, urokinase, trypsin, etc. may be used. As indicated earlier t-PA and plasmin are preferred.

It is also to be understood that the present invention is not limited to monoclonal antibodies in the immunoassay. Thus, any antibody that is specific for D-dimer rather than for fibrinogen or fibrin may be used. As stated earlier, an appropriate monoclonal antibody is preferred however. With respect to the kit claims hereinafter it is known that immunoassay kits are of two types, the first being a direct assay which employs the sandwich approach. These kits contain a set of standards, a first antibody (i.e. capture antibody) usually immobilized on a surface and a second antibody labeled with a signal generator. The label can be any detectable entity such as radioactive, an enzyme, fluorophore, chemiphore, etc. The second type of immunoassay is the competitive type. These kits contain standards, labeled antigen and specific antibody. The kits may also contain specific buffers, substrates, separating agents and controls. The kits may contain collection devices or chemicals to treat the patient sample listed hereinbefore. In this invention the specimen could be plasma and could be drawn by conventional techniques. This kit would contain a plasminogen activator or active plasmin to treat the specimen (sample).

What is claimed is:

1. A process for the in vitro determination of crosslinked soluble fibrin polymers in a patient sample which comprises contacting said sample with at least one proteolytic enzyme to generate the D-dimer fragment of said fibrin polymers and measuring the amount of said D-dimer.

2. A process for the in vitro determination of crosslinked soluble fibrin polymers in a patient sample which comprises
   (a) adding a plasminogen activator to said sample, wherein said plasminogen activator activates endogenous fibrin-bound plasminogen and converts the plasminogen to plasmin;
   (b) contacting said sample with exogenous plasminogen to generate the D-dimer fragment of said fibrin polymers; and
   (c) measuring the amount of said D-dimer.

3. The process according to claim 1 in which the proteolytic enzyme is plasminogen.

4. The process according to claim 1 in which the proteolytic enzyme is a plasminogen activator.

5. The process according to claim 1 in which the proteolytic enzymes are plasminogen and a plasminogen activator.

6. The process according to any one of claims 2, 4 or 5 in which the plasminogen activator is tissue plasminogen activator.

7. The process according to claim 2 or 5 in which an effective amount of the plasminogen is from about 1 unit/ml to about 10 units/ml.

8. The process according to claim 1 or 2 in which the amount of said D-dimer is measured by an immunoassay specific to said D-dimer.

9. The process according to claim 8 in which an antibody that is reactive with D-dimer preferentially over fibrin polymers is used in said immunoassay.

10. The process according to claim 8 in which a monoclonal antibody is used in said immunoassay to bind said D-dimer.

11. The process of claim 10 in which the monoclonal antibody is DD/3B6/22.

12. The process of claim 1 or 2 in which the amount of said D-dimer is measured by gel electrophoresis, thin-layer chromatography, or column chromatography.

13. A diagnostic kit for assaying the amount of D-dimer in a patient sample comprising a carrier being compartmented to receive a series of containers in close confinement which comprises:
    (a) a first container containing a measured amount of standard containing crosslinked soluble fibrin polymers,
    (b) a second container containing a measured amount of a proteolytic enzyme, and
    (c) A third container containing an antibody specific to said D-dimer.

14. A kit according to claim 13 in which the antibody is a monoclonal antibody.

15. A kit according to claim 13 in which the monoclonal antibody is DD/3B6/22.

16. A kit according to claim 13 in which the proteolytic enzyme is tissue plasminogen activator.

17. A kit according to claim 13 in which the proteolytic enzyme is plasmin.

* * * * *

UNITED STATES PATENT AND TRADEMARK OFFICE
CERTIFICATE OF CORRECTION

PATENT NO. : 5,206,140
DATED : April 27, 1993
INVENTOR(S) : Victor J. Marder, et al.

It is certified that error appears in the above-indentified patent and that said Letters Patent is hereby corrected as shown below:

```
Column 4, line 58:    "mg.ml"   should read --mg/ml--
Column 5, line 23:    "ere"     should read --were--
Column 5, line 59:    "hours"   should read --hour--
Column 5, line 67:    "PH"      should read --pH--
Column 6, line 10:    "palte"   should read --plate--
```

Signed and Sealed this

Eighteenth Day of January, 1994

Attest:

BRUCE LEHMAN

*Attesting Officer*   *Commissioner of Patents and Trademarks*